US012734224B2

(12) United States Patent
Sun et al.

(10) Patent No.: US 12,734,224 B2
(45) Date of Patent: Sep. 15, 2026

(54) RECOMBINANT PROTEIN CAPABLE OF RESISTING MULTIPLE SCLEROSIS AND PREPARATION METHOD AND APPLICATION THEREOF

(71) Applicant: INSTITUTE OF ZOOLOGY, GUANGDONG ACADEMY OF SCIENCES, Guangzhou (CN)

(72) Inventors: Yunxiao Sun, Guangzhou (CN); Junhua Rao, Guangzhou (CN); Dainan Cao, Guangzhou (CN); Zhen Peng, Guangzhou (CN); Libiao Zhang, Guangzhou (CN); Bihai Li, Guangzhou (CN); Xiangyang He, Guangzhou (CN); Fang Ji, Guangzhou (CN)

(73) Assignee: INSTITUTE OF ZOOLOGY, GUANGDONG ACADEMY OF SCIENCES, Guangzhou (CN)

( * ) Notice: Subject to any disclaimer, the term of this patent is extended or adjusted under 35 U.S.C. 154(b) by 354 days.

(21) Appl. No.: 18/398,273

(22) Filed: Dec. 28, 2023

(65) Prior Publication Data

US 2024/0197847 A1 Jun. 20, 2024

Related U.S. Application Data

(63) Continuation of application No. PCT/CN2022/082141, filed on Mar. 22, 2022.

(30) Foreign Application Priority Data

Jul. 5, 2021 (CN) ........................ 202110759727.8

(51) Int. Cl.

| | |
|---|---|
| ***A61K 39/00*** | (2006.01) |
| ***A61P 25/28*** | (2006.01) |
| ***A61P 37/06*** | (2006.01) |
| ***C07K 14/47*** | (2006.01) |
| ***C12N 15/70*** | (2006.01) |
| ***C12P 21/02*** | (2006.01) |

(52) U.S. Cl.

CPC .......... *A61K 39/0008* (2013.01); *A61P 25/28* (2018.01); *A61P 37/06* (2018.01); *C07K 14/47* (2013.01); *C12N 15/70* (2013.01); *C12P 21/02* (2013.01); *A61K 2039/543* (2013.01)

(58) Field of Classification Search

CPC .......... A61K 39/0008; A61K 2039/543; A61P 25/28; A61P 37/06; C07K 14/47; C12N 15/70; C12P 21/02

See application file for complete search history.

(56) References Cited

U.S. PATENT DOCUMENTS 6,495,347 B1 * 12/2002 Siegel ................ G01N 33/5047 435/69.7
2005/0031649 A1 2/2005 Yu et al.

FOREIGN PATENT DOCUMENTS

| | | | |
|---|---|---|---|
| CN | 1831012 | A | 9/2006 |
| CN | 105254765 | A | 1/2016 |
| CN | 105296408 | A | 2/2016 |
| CN | 108611310 | A | 10/2018 |
| CN | 110719787 | A | 1/2020 |
| CN | 113336862 | A | 9/2021 |
| WO | 2020010221 | A1 | 1/2020 |

OTHER PUBLICATIONS

Rezende et al., Hsp65-producing Lactococcus lactis prevents experimental autoimmune encephalomyelitis in mice by inducing CD4 +Lap+ regulatory T cells; J Autoimmun. Feb. 2013; 40: 45-57, doi: 10.1016/j.jaut.2012.07.012. Epub Aug. 28, 2012. PMID: 22939403; PMCID: PMC3623677. (Year: 2013).*

International Search Report issued in corresponding International application No. PCT/CN2022/082141, mailed Jun. 21. 2022 (10 pages).

Written Opinion of the International Search Authority in corresponding International application No. PCT/CN2022/082141, mailed Jun. 21, 2022 (6 pages).

* cited by examiner

*Primary Examiner* — Louise W Humphrey
*Assistant Examiner* — Rachel Emily Martin
(74) *Attorney, Agent, or Firm* — HOWARD M COHN and Associates, LLC

(57) ABSTRACT

The present invention discloses a recombinant protein capable of resisting multiple sclerosis and a preparation method and application thereof, and belongs to the technical field of biopharmacy. The recombinant protein of the present invention comprises *Mycobacterium tuberculosis* heat shock protein 65 and 6-segment tandem repeat myelin oligodendroglia glycoprotein antigen epitope polypeptides with multiple sclerosis autoimmune antigen characteristics at the 33rd-55th sites. The recombinant protein capable of resisting multiple sclerosis is used for preparing multiple sclerosis vaccines and/or preparing multiple sclerosis drugs. The present invention can play a role in preventing multiple sclerosis and can avoid side effects caused by most of disease modifying therapy (DMT) drugs.

4 Claims, 15 Drawing Sheets
(5 of 15 Drawing Sheet(s) Filed in Color)
Specification includes a Sequence Listing.

1 2 3

SEQUENCE LISTING

```
Sequence total quantity: 1
SEQ ID NO: 1           moltype = AA  length = 691
FEATURE                Location/Qualifiers
source                 1..691
                       mol_type = protein
                       organism = synthetic construct
SEQUENCE: 1
MGSSHHHHHH SSGAKTIAYD EEARRGLERG LNALADAVKV TLGPKGRNVV LEKKWGAPTI  60
TNDGVSIAKE IELEDPYEKI GAELVKEVAK KTDDVAGDGT TTATVLAQAL VREGLRNVAA  120
GANPLGLKRG IEKAVEKVTE TLLKGAKEVE TKEQIAATAA ISAGDQSIGD LIAEAMDKVG  180
NEGVITVEES NTFGLQLELT EGMRFDKGYI SGYFVTDPER QEAVLEDPYI LLVSSKVSTV  240
KDLLPLLEKV IGAGKPLLII AEDVEGEALS TLVVNKIRGT FKSVAVKAPG FGDRRKAMLQ  300
DMAILTGGQV ISEEVGLTLE NADLSLLGKA RKVVVTKDET TIVEGAGDTD AIAGRVAQIR  360
QEIENSDSDY DREKLQERLA KLAGGVAVIK AGAATEVELK ERKHRIEDAV RNAKAAVEEG  420
IVAGGGVTLL QAAPTLDELK LEGDEATGAN IVKVALEAPL KQIAFNSGLE PGVVAEKVRN  480
LPAGHGLNAQ TGVYEDLLAA GVADPVKVTR SALQNAASIA GLFLTTEAVV ADKPEKEKAS  540
VPGGGDMGGM DFASAMEVGW YRSPFSRVVH LYRNGKSSME VGWYRSPFSR VVHLYRNGKS  600
SMEVGWYRSP FSRVVHLYRN GKSSMEVGWY RSPFSRVVHL YRNGKSSMEV GWYRSPFSRV  660
VHLYRNGKSS MEVGWYRSPF SRVVHLYRNG K                                 691
```

RECOMBINANT PROTEIN CAPABLE OF RESISTING MULTIPLE SCLEROSIS AND PREPARATION METHOD AND APPLICATION THEREOF

SEQUENCE LISTING

The instant application contains a Sequence Listing which has been submitted electronically in ST.26 format and is hereby incorporated by reference in its entirety. Said ST.26 copy, created on Dec. 25, 2023, is named Sequence Listing.xml and is 2440 bytes in size.

TECHNICAL FIELD

The present invention relates to the technical field of biopharmacy, and particularly relates to a recombinant protein capable of resisting multiple sclerosis and a preparation method and application thereof.

BACKGROUND

Multiple sclerosis (MS) is an autoimmune inflammatory neurodegenerative disease characterized by demyelination of the central nervous system. The clinical manifestations of MS include sensory loss, muscle weakness, dysphrasia, dizziness, dyskinesia and even paralysis. Different symptoms depend on the lesion sites of the brain and spinal cord. So far, there is no effective method for curing MS. Disease modifying therapy (DMT) drugs are commonly used in the treatment of MS clinically. The existing DMT drugs currently include: first-line drugs such as interferon (IFN-β 1b and IFN-β 1a) and glatiramer acetate (GA); and second-line drugs such as dimethyl fumarate, fingolimod, teriflunomide, mitoxantrone, natalizumab, alemtuzumab, etc. However, this treatment method only reduces the recurrence rate of the disease and delays the progression of the disease. In addition, these drugs are usually ineffective in patients with severe MS and bring strong side effects.

MS is an autoimmune disease characterized by inflammatory demyelination disease of white matter in the central nervous system, and antigen-specific vaccines that induce myelin-specific immune tolerance are expected to be safe and effective treatment drugs for MS. The autoimmune disease refers to the disease caused by the damage to autologous tissue due to the immune response of the body to the autoantigen. In the research of prevention of the autoimmune disease, the development of the vaccines by the autoantigen is an attractive method currently. Myelin oligodendrocyte glycoprotein (MOG) is one of the main autoantigens that induce MS, and there are three encephalitis antigen epitopes in the extracellular region. $MOG_{35-55}$ (35MEVGWYRSPFSRVVHLYRNGK55) is a section of polypeptide formed by 21 amino acids in MOG, is the key antigen epitope, and can induce C57BL/6 mice to generate typical chronic-non palliative experimental autoimmune encephalomyelitis (EAE) symptoms. The EAE model of C57BL/6 mice induced by $MOG_{35-55}$ antigen peptide is the classic MS animal model that is widely used currently. The autoantigen plays the role of a double-edged sword in the autoimmune disease. On the one hand, the autoantigen is the inducement that mediates the occurrence of the disease and plays a key role in the occurrence and development of the disease. On the other hand, if appropriate immune strategies are adopted, such as immunization of autoantigen through appropriate ways, doses and cycles, immune responses to the autoantigen can be adjusted pointedly to induce the body to produce immune tolerance or benign regulatory immune response, thereby achieving the effect of preventing the autoimmune disease.

In view of this, it is necessary to study an antigen peptide containing $MOG_{35-55}$ which can replace the existing DMT drugs, which can produce immune tolerance to the autoantigen by changing the immune mode and inducing targeted immunoregulation for resisting multiple sclerosis.

SUMMARY

A purpose of the present invention is to propose a recombinant protein capable of resisting multiple sclerosis, and a preparation method and application thereof. The recombinant protein comprises HSP65 protein and $MOG_{35-55}$ protein and can play a role in preventing multiple sclerosis.

Another purpose of the present invention is to propose a preparation method of the recombinant protein capable of resisting multiple sclerosis. The preparation method has strong reliability.

Another purpose of the present invention is to propose an application of the recombinant protein capable of resisting multiple sclerosis. The protein is used for preparing multiple sclerosis vaccines and/or preparing multiple sclerosis drugs, and can achieve a good effect.

Another purpose of the present invention is to propose an administration method of the above multiple sclerosis vaccines or multiple sclerosis drugs. The administration method is intranasal administration, and is safe and effective.

To achieve the purposes, the present invention adopts the following technical solution:

A recombinant protein capable of resisting multiple sclerosis is provided, comprising HSP65 protein and antigen epitope polypeptide $MOG_{35-55}$ protein.

Further, the recombinant protein comprises an HSP65 protein and 6-segment tandem repeat antigen epitope polypeptide $MOG_{35-55}$ protein, i.e., the recombinant protein comprises HSP65 and $6MOG_{35-55}$.

Further, the HSP65 protein and the 6-segment tandem repeat antigen epitope polypeptide $MOG_{35-55}$ protein are connected through a flexible joint.

Further, the HSP65 protein and the 6-segment tandem repeat antigen epitope polypeptide $MOG_{35-55}$ protein are connected through an Ala-Ser-Ala flexible joint.

Further, a sequence of the recombinant protein is SEQ ID NO.1.

A preparation method of the recombinant protein capable of resisting multiple sclerosis is provided. The method is used for preparing the above recombinant protein capable of resisting multiple sclerosis. The method comprises the following steps:

(1) building a recombinant plasmid pET28a-His-HSP65-$6MOG_{35-55}$ to obtain engineering bacteria having the recombinant plasmid;

(2) culturing the engineering bacteria with an LB culture medium; when the bacteria reach a logarithmic growth period, adding a sterile lactose solution of 0.5 mol/L into the culture medium until a final concentration is 5 mmol/L; and after further culture for 7 hours, collecting the bacteria;

(3) separating fusion protein and purifying the fusion protein by the collected bacteria to obtain the recombinant protein capable of resisting multiple sclerosis.

Further, the step (1) comprises the following steps:

inserting a codon of $6MOG_{35-55}$ into pET-28a(+) to obtain the plasmid pET28a-$6MOG_{35-55}$;

conducting PCR amplification on a template of the plasmid pET28a-$6MOG_{35-55}$ to obtain a target gene segment for encoding $6MOG_{35-55}$ sequence;

conducting NheI and HindIII double digestion on a pET28a-His-HSP65-6P277 vector to obtain a linearized cloning vector;

recombining the target gene segment for encoding $6MOG_{35-55}$ sequence and the linearized cloning vector to obtain the recombinant plasmid; transforming the recombinant plasmid into a competent cell and selecting a positive clone by PCR; and verifying the obtained positive clone to finally obtain the engineering bacteria having the recombinant plasmid.

Further, in the step (3):

lysing the collected bacteria and ultrasonically breaking the bacteria on ice; analyzing the supernatant and precipitate respectively and determining that the fusion protein is an inclusion body;

processing the inclusion body with an inclusion body solution containing urea;

collecting the supernatant; and purifying the target protein with Ni-NTA agarose gel column to obtain the recombinant protein His-HSP65-$6MOG_{35-55}$.

The recombinant protein capable of resisting multiple sclerosis is used for preparing multiple sclerosis vaccines and/or preparing multiple sclerosis drugs.

Further, the multiple sclerosis vaccines or multiple sclerosis drugs are administered intranasally.

Embodiments of the present invention have the following beneficial effects:

The recombinant protein comprises HSP65 protein and $MOG_{35-55}$ protein. An EAE mouse model can well reflect the immune reactivity of tubercle *Bacillus* HSP65 and human HSP60. HSP65 is used as a molecular chaperone, can also be used as a molecular carrier to assist T cell epitope and is recognized by MHCII molecules of antigen-presenting cells, there stimulating the differentiation and proliferation of CD4+ cells in the body. Heat shock protein also has the role of an adjuvant. For example, HSP acts as an immune danger signal to activate natural immunity, and stimulates DC to up-regulate MHC (class I and II) and costimulatory molecule levels. In addition, HSP receptors exist on the surface of macrophage, DC and NK cells, and HSP can bind to the receptor on APC. Antigenic peptides are delivered onto the APC surface through MHC-I to induce specific immune responses and play the role of immunoregulation in cell-mediated immune responses.

To improve immunogenicity of $MOG_{35-55}$, in the present invention, $MOG_{35-55}$ is subjected to 6 tandem repeats, which can give full play to the immune effect of amino acid fragment. The flexible joint Ala-Ser-Ala is added between HSP65 and 6 $MOG_{35-55}$ to ensure that HSP65 can be correctly folded.

DESCRIPTION OF DRAWINGS

The present disclosure contains at least one drawing executed in color. Copies of this patent or patent application publication with color drawing(s) will be provided by the Office upon request and payment of the necessary fee.

DETAILED DESCRIPTION

Figure 1:
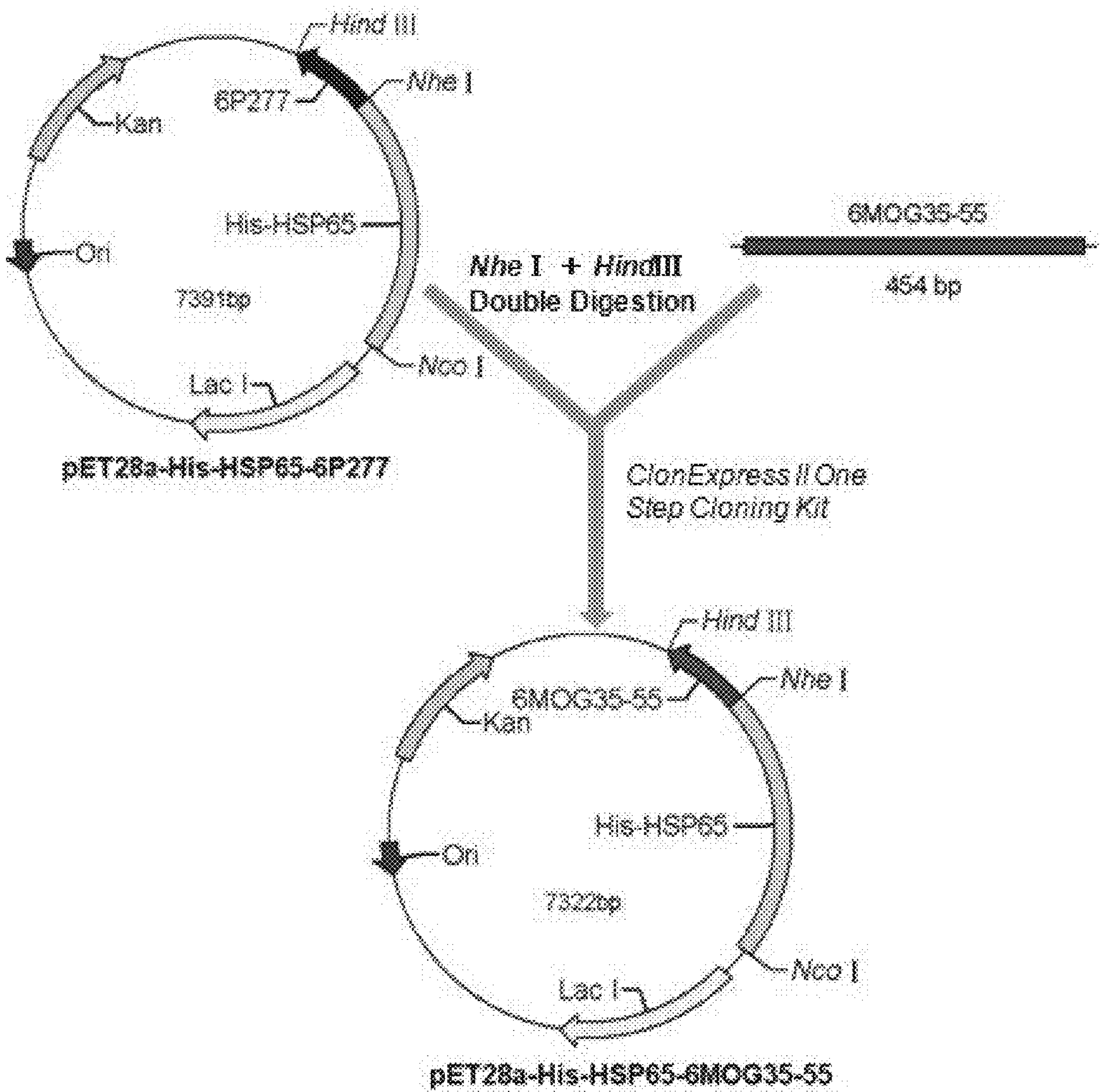
FIG. 1 is a schematic diagram of construction of pET28a-His-HSP65-$6MOG_{35-55}$ recombinant protein vector plasmid.

Heat shock protein 65 (HSP65) is also reported as one of the autoantigens of autoimmune disease EAE. HSP60/65 family of the heat shock protein is highly conserved. *Mycobacterium tuberculosis* HSP65 (MT-HSP65) has about 50% homology with human HSP60, and rat HSP60 molecule and human HSP60 molecule have 97% homology at amino acid level. Therefore, the present invention provides a recombinant protein capable of resisting multiple sclerosis, and the recombinant protein comprises HSP65 protein and antigen epitope polypeptide $MOG_{35-55}$. An EAE mouse model can well reflect the immune reactivity of MT-HSP65 and human HSP60.

HSP65 is used as a molecular chaperone, can also be used as a molecular carrier to assist T cell epitope and is recognized by MHCII molecules of antigen-presenting cells, there stimulating the differentiation and proliferation of CD4+ cells in the body. Heat shock protein also has the role of an adjuvant. For example, HSP acts as an immune danger signal to activate natural immunity, and stimulates DC to up-regulate MHC (class I and II) and costimulatory molecule levels. In addition, HSP receptors exist on the surface of macrophage, DC and NK cells, and HSP can bind to the receptor on APC. Antigenic peptides are delivered onto the APC surface through MHC-I to induce specific immune responses and play the role of immunoregulation in cell-mediated immune responses.

Further, the recombinant protein comprises an HSP65 protein and 6-segment tandem repeat antigen epitope polypeptide $MOG_{35-55}$, i.e., the recombinant protein comprises HSP65 and $6MOG_{35-55}$. To improve immunogenicity of $MOG_{35-55}$, in the present invention, $MOG_{35-55}$ is subjected to 6 tandem repeats, which can give full play to the immune effect of amino acid fragment.

Further, the HSP65 protein and the 6-segment tandem repeat antigen epitope polypeptide $MOG_{35-55}$ are connected through a flexible joint. Specifically, adjacent $MOG_{35-55}$ are separated and connected by two serines (Ser-Ser), and then fused with HSP65 carboxyl terminal. A flexible joint Ala-Ser-Ala is added in the middle to ensure that HSP65 can be correctly folded.

Further, a sequence of the recombinant protein is SEQ ID NO.1.

Correspondingly, the present invention also provides a preparation method of the recombinant protein capable of resisting multiple sclerosis. The method is used for preparing the above recombinant protein capable of resisting multiple sclerosis. The method comprises the following steps:

(1) building a recombinant plasmid pET28a-His-HSP65-$6MOG_{35-55}$ to obtain engineering bacteria having the recombinant plasmid;
(2) culturing the engineering bacteria with an LB culture medium; when the bacteria reach a logarithmic growth period, adding a sterile lactose solution of 0.5 mol/L into the culture medium until a final concentration is 5 mmol/L; and after further culture for 7 hours, collecting the bacteria;
(3) separating fusion protein and purifying the fusion protein by the collected bacteria to obtain the recombinant protein capable of resisting multiple sclerosis.

In the above method, a good proliferation effect and large amount of target protein expression are achieved through induction at a concentration of 5 mmol/L lactose and continuous culture for 7 hours after the induction.

Further, the step (1) comprises the following steps:

inserting a codon of $6MOG_{35-55}$ into pET-28a(+) to obtain the plasmid pET28a-$6MOG_{35-55}$;
conducting PCR amplification on a template of the plasmid pET28a-$6MOG_{35-55}$ to obtain a target gene segment for encoding $6MOG_{35-55}$ sequence;
conducting NheI and HindIII double digestion on a pET28a-His-HSP65-6P277 vector to obtain a linearized cloning vector;
recombining the target gene segment for encoding $6MOG_{35-55}$ sequence and the linearized cloning vector to obtain the recombinant plasmid; transforming the recombinant plasmid into a competent cell and selecting a positive clone by PCR; and verifying the obtained positive clone to finally obtain the engineering bacteria having the recombinant plasmid.

The engineering bacteria having the recombinant plasmid pET28a-His-HSP65-$6MOG_{35-55}$ can be accurately obtained through the above preparation method of the engineering bacteria having the recombinant plasmid, to reduce operation difficulty.

Further, in the step (3):

lysing the collected bacteria and ultrasonically breaking the bacteria on ice; analyzing the supernatant and precipitate respectively and determining that the fusion protein is an inclusion body;
processing the inclusion body with an inclusion body solution containing urea;
collecting the supernatant; and purifying the target protein with Ni-NTA agarose gel column to obtain the recombinant protein His-HSP65-$6MOG_{35-55}$.

Through the above lysing method and purification method, high-purity recombinant protein is obtained while ensuring the conformation of the protein.

The recombinant protein capable of resisting multiple sclerosis is used for preparing multiple sclerosis vaccines and/or preparing multiple sclerosis drugs.

A large number of studies prove that MOG and related antigenic peptides can induce and aggravate EAE symptoms in mice by subcutaneous immunization. Further, the multiple sclerosis vaccines or multiple sclerosis drugs are administered intranasally.

The mucosa gives autoantigens to induce immune tolerance, which is an effective way to prevent autoimmune diseases. Nasal mucosa is an important part of the mucosal immune system. Nasal mucosal immunity is an attractive way. Because abundant blood vessels are contained in the nasal cavity, mucosal immunity and systemic immunity can be generated through intranasal inoculation. The nasal cavity contains less proteolytic enzymes and the same small dose of antigen can be delivered more effectively to stimulate the mucosal immune system. Inoculation is easy to operate, does not need special instruments such as syringes, easy to be accepted by a large number of people, and can avoid cross infection caused by injection. In addition, intranasal immune can significantly reduce the use amount of immunogen, and is a safe and effective immune way. In this study, nasal mucosal immunity is used to induce specific immune tolerance responses to achieve the purpose of effectively preventing EAE/MS.

The recombinant protein capable of resisting multiple sclerosis and the preparation method thereof in embodiments of the present invention are described below in combination with FIGS. 1-12.

I. Material

Strains, Plasmids and Animals

Host bacteria *Escherichia coli* BL21 (DE3) are common tool strains of genetic engineering, and plasmid pET28a is common cloning vector in genetic engineering and is purchased from Tiangen Biotech (Beijing) Co., Ltd. C57BL/6 mice, 6-8 weeks old, female, 16-20 g in weight, purchased from Guangdong Medical Laboratory Animal Center.

$MOG_{35-55}$ polypeptide (MEVGWYRSPFSRVVHLYRNGK) used for preparation of mouse EAE/MS disease model is synthesized by GL Biochem (Shanghai) Ltd., with synthesis purity of greater than 99.39%

Enzymes and Main Reagents

Molecular cloning tool enzymes are purchased from TaKaRa; PCR purification kit is from Promega company;

pertussis toxin (PTX) is purchased from Enzo of the United States; and complete Freund's adjuvant (CFA) is purchased from Sigma.

Plasmid Vector $6MOG_{35-55}$ is synthesized by Shanghai Generay Biotech Co., Ltd. by optimizing and synthesizing $6MOG_{35-55}$ gene sequence codons according to the dominant codons of *Escherichia coli* and reverse-inserting the gene sequence codons into the cloning vector of pET-28a(+) to obtain pET28a-$6MOG_{35-55}$. pET28a-HSP65-6p277 is stored and presented by Wegene laboratory of China Pharmaceutical University.

II. Construction of Recombinant Plasmids pET28a-his-HSP65-$6MOG_{35-55}$ and Corresponding Recombinant Engineering Bacteria The construction idea of recombinant plasmids pET28a-His-HSP65-$6MOG_{35-55}$ is selection of appropriate digestion sites according to requirements, and the specific construction process is shown in FIG. 1.

Firstly, the plasmids pET28a-$6MOG_{35-55}$ are obtained as follows: digestion sites NheI and HindIII are designed on both sides of $6MOG_{35-55}$ gene sequence by Shanghai Generay Biotech Co., Ltd., and the codons are optimized and synthesized according to the dominant codons of *Escherichia coli* and reverse-inserted into the cloning vector of pET-28a(+) to obtain plasmids pET28a-$6MOG_{35-55}$.

The plasmids pET28a-His-HSP65-6P277 are extracted with the plasmid extraction kit of Sangon. The plasmids are subjected to NheI and HindIII double digestion, and gel extraction to obtain a large fragment of plasmids (linearized cloning vector), which is verified by agarose gel electrophoresis.

PCR amplification is obtained by inserting a small fragment of $6MOG_{35-55}$: a linearized cloning vector terminal homologous sequence is introduced into the 5' end of a primer, so that two ends of the PCR product of the inserted fragment have a sequence (15-20 bp) which is consistent with the two ends of the linearized cloning vector. Primers are synthesized by Sangon Biotech (Shanghai) Co., Ltd. Two oligonucleotide sequences of the primers are as follows (NheI and HindIII digestion sites in bold black):

```
P1:
GGTGGCATGGATTTCGCTAGCGCAATGGAAGTAGGTTGGTATAGATC

P2:
CTCGAGTGCGGCCGCAAGCTTATTTACC
```

PCR is conducted by using P1 as a forward primer, P2 as a reverse primer and pET28a-$6MOG_{35-55}$ plasmid as a template to obtain the coding sequence $6MOG_{35-55}$ of small fragment of target gene. After ligation recombination and transformation of the obtained large and small fragments, the positive clone is verified through PCR detection. The forward primer and the reverse primer used for screening the positive clone by PCR are: forward primer V1: CAGAATGCGGCGTCCAT, and reverse primer V2: CCTTTCGGGCTTTGTTAGCAG.

The correct positive clone bacteria solution verified by colony PCR is cultured overnight, and the plasmid is extracted for double digestion verification. The correct positive clone is selected and sent to Sangon Biotech (Shanghai) Co., Ltd. for sequencing. Sequencing results are shown in FIG. 3A-FIG. 3G. The sequence is completely correct after comparison, and thus *Escherichia coli* BL21 expression bacteria (engineering bacteria with recombinant plasmids) carrying recombinant plasmids pET28a-His-HSP65-$6MOG_{35-55}$ are successfully constructed.

Figure 2A:
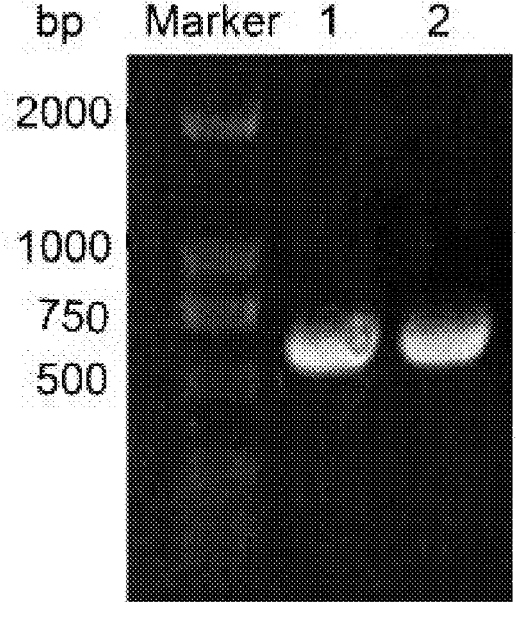
FIG. 2A shows 1% agarose gel sugar electrophoresis analysis of positive monoclonal plasmid PCR product.
Figure 2B:
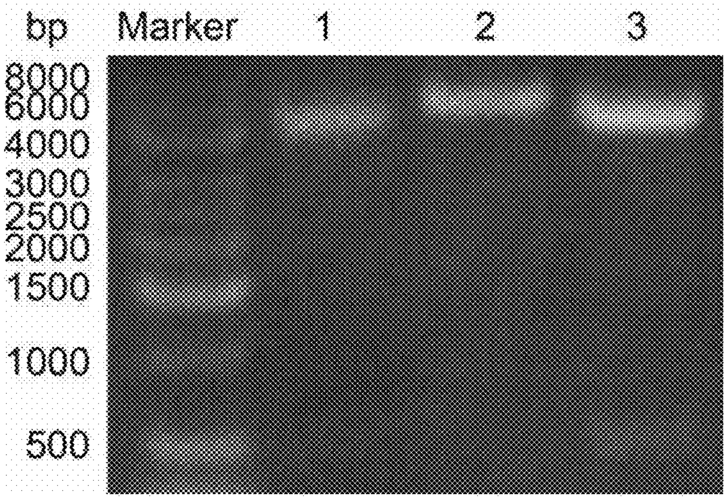
FIG. 2B shows 1% agarose gel sugar electrophoresis analysis of positive plasmid and plasmid enzyme digestion product.
Figure 3A:
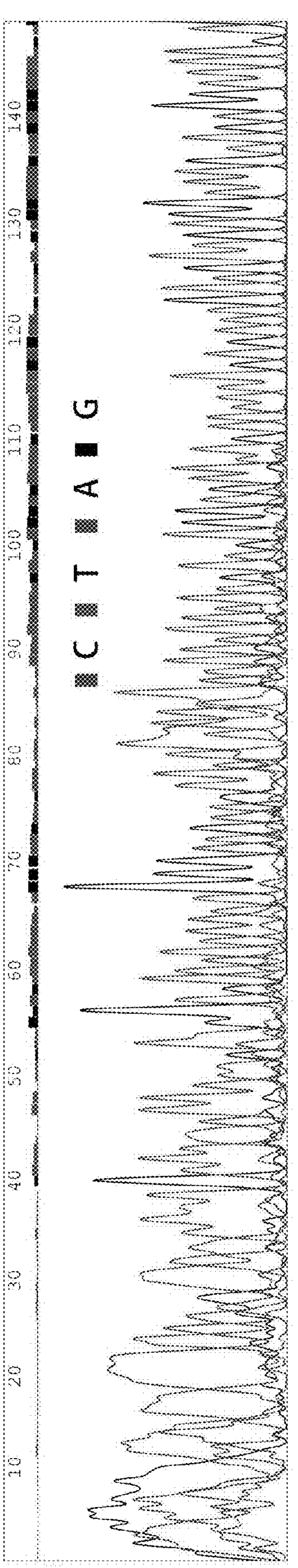
FIG. 3A is a diagrams of a first section of a sequencing diagram of target protein encoding genes in recombinant plasmid pET28a-His-HSP65-$6MOG_{35-55}$.
Figure 3B:
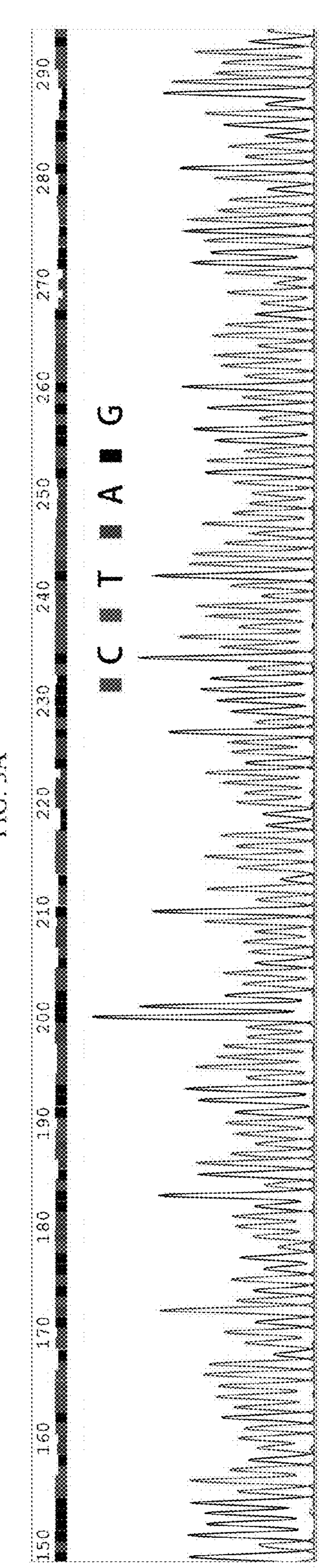
FIG. 3B is a diagrams of a second section of the sequencing diagram of the target protein encoding genes in recombinant plasmid pET28a-His-HSP65-$6MOG_{35-55}$.
Figure 3C:
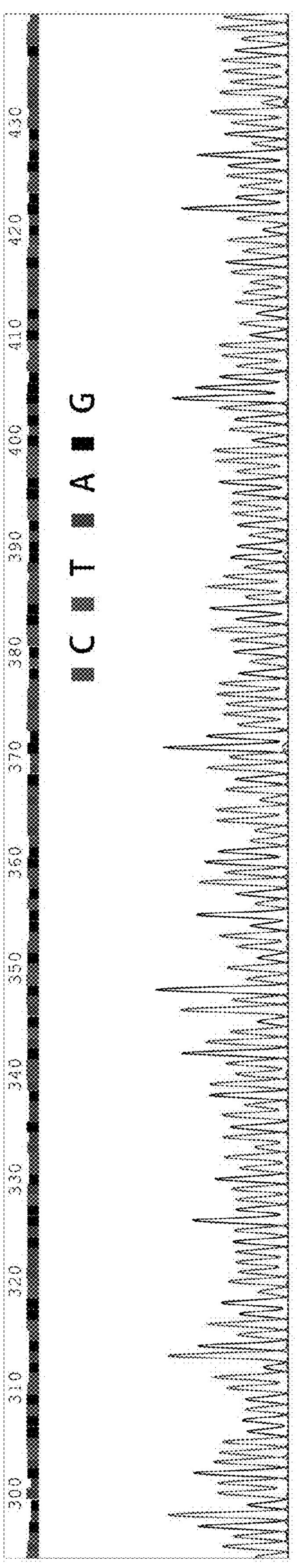
FIG. 3C is a diagrams of a third section of the sequencing diagram of the target protein encoding genes in recombinant plasmid pET28a-His-HSP65-$6MOG_{35-55}$.
Figure 3D:
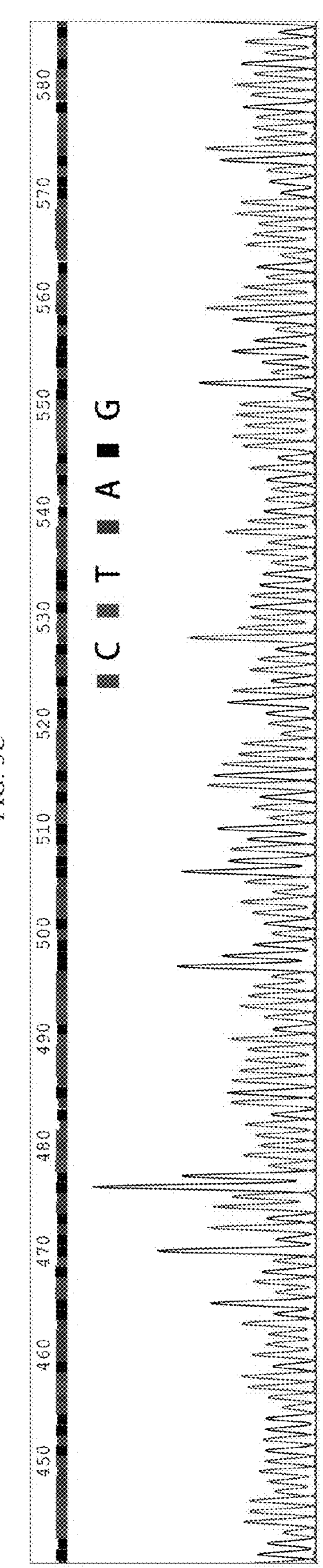
FIG. 3D is a diagrams of a fourth section of the sequencing diagram of the target protein encoding genes in recombinant plasmid pET28a-His-HSP65-$6MOG_{35-55}$.
Figure 3E:
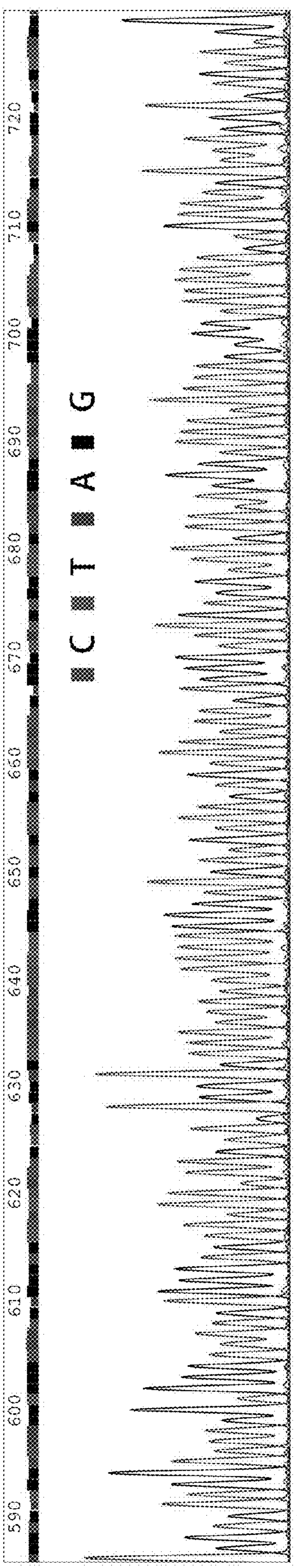
FIG. 3E is a diagrams of a fifth section of the sequencing diagram of the target protein encoding genes in recombinant plasmid pET28a-His-HSP65-$6MOG_{35-55}$.
Figure 3F:
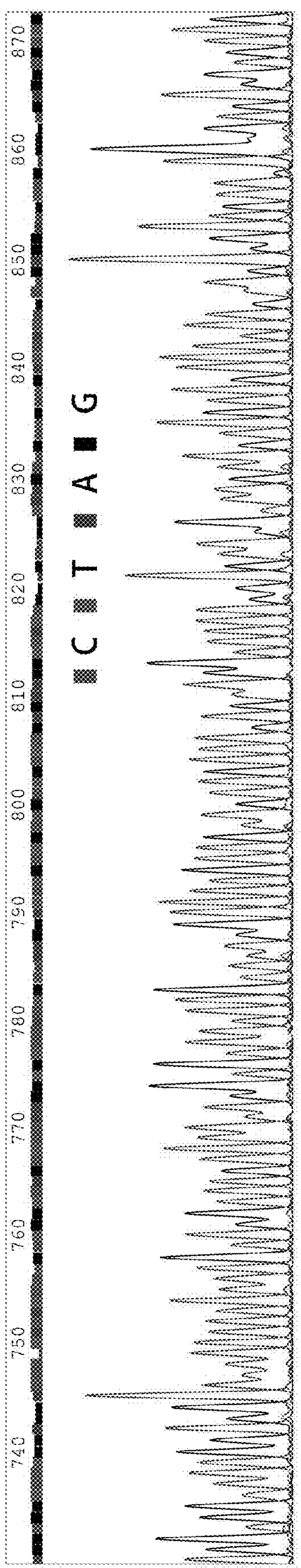
FIG. 3F is a diagrams of a sixth section of the sequencing diagram of the target protein encoding genes in recombinant plasmid pET28a-His-HSP65-$6MOG_{35-55}$.
Figure 3G:
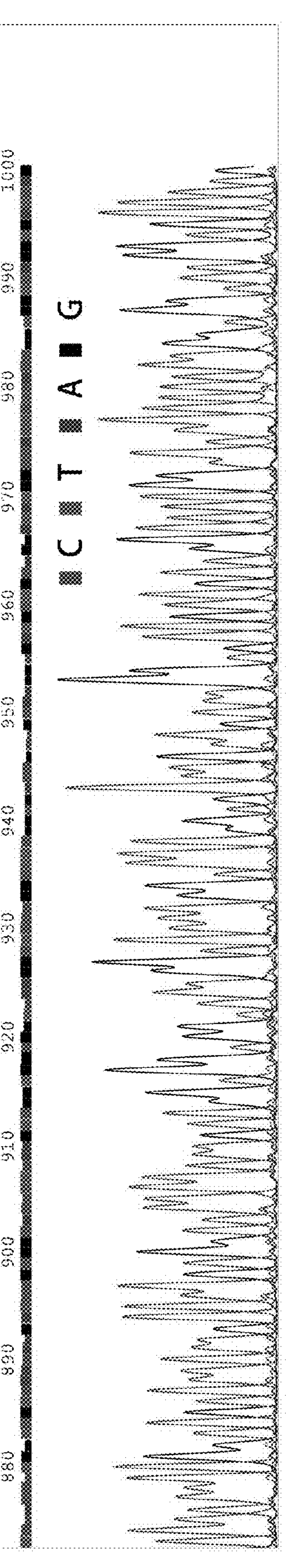
FIG. 3G is a diagrams of a seventh section of the sequencing diagram of the target protein encoding genes in recombinant plasmid pET28a-His-HSP65-$6MOG_{35-55}$.

Appropriate identification primers V1 and V2 are designed at about 100 bp upstream and downstream of the insertion digestion site. As shown in FIG. 2A, the PCR products of positive monoclones 1.2 are consistent with the actual size of 605 bp and can be used for further enzyme digestion identification. As shown in FIG. 2B, the plasmid pET28a-His-Hsp65-$6MOG_{35-55}$ is 7322 bp in size, and there is a single band between 6000-8000 kb after single digestion by HindIII, which is consistent with the actual size. After double digestion by NheI and HindIII, a 418 bp fragment is cut, and the band can be vaguely seen at 500 bp. The linear plasmids after double digestion run obviously in the earlier positions than the plasmids after single digestion, indicating that the target gene is linked into the vector. In FIG. 2A, lanes 1-2 show the PCR products of positive clone plasmids; and in FIG. 2B, lane 1 shows the complete plasmid of pET28a-His-HSP65-$6MOG_{35-55}$, lane 2 shows a single digestion product of Hind III of pET28a-His-Hsp65-$6MOG_{35-55}$ plasmid, and lane 3 shows a double digestion product of Nhe I and Hind III of the pET28a-His-Hsp65-$6MOG_{35-55}$ plasmid.

Figure 4:
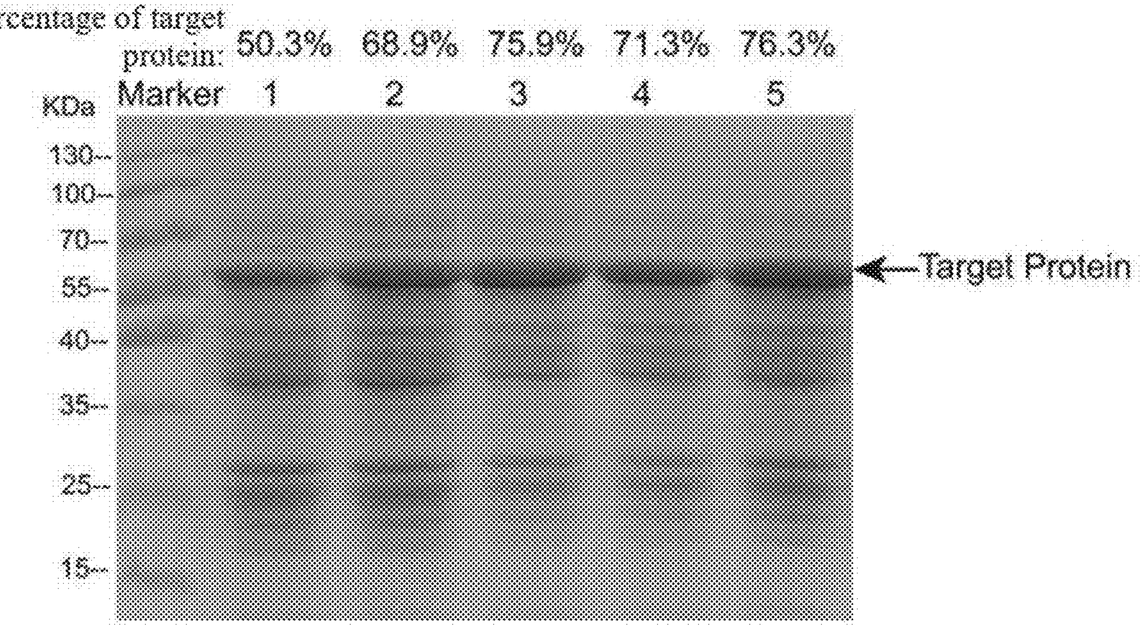
FIG. 4 is a diagram of expression levels of target protein His-HSP65-$6MOG_{35-55}$ after lactose induction of different concentrations by 12% SDS-PAGE electrolysis.

III. Determination of Optimum Lactose Induction Concentration of Target Protein The engineering bacteria with recombinant plasmids are inoculated into fresh LB culture medium (containing 50 μg/mL Kan) for shaking culture at constant temperature of 37° C. When the bacteria grow to a logarithmic growth period (after inoculation for 3-4 h, OD600 nm is about 0.6), a sterile lactose solution of 0.5 mol/L is added so that the final lactose concentrations of all bottles are 1 mmol/L, 3 mmol/L, 5 mmol/L, 7 mmol/L and 9 mmol/L respectively. After induction for 6 h, 1 ml of samples are taken to connect the bacteria by centrifugation, and 12% SDS-PAGE protein electrophoresis is conducted to determine the optimum lactose induction concentration. BandScan5.0 image analysis software is used to analyze the electrophoretogram. In FIG. 4, lanes 1-5 show the expression levels of target protein after lactose induction at 1 mM, 3 mM, 5 mM, 7 mM and 9 mM, respectively. As shown in FIG. 4, there is no significant difference in induction between the final concentrations of 5 mM lactose (lane 3, 75.9%) and 9 mM lactose (lane 5, 76.3%), so the final concentration of 5 mM lactose is determined as the optimum induction concentration of lactose.

IV. Determination of Optimum Induction Time of Target Protein

Figure 5:
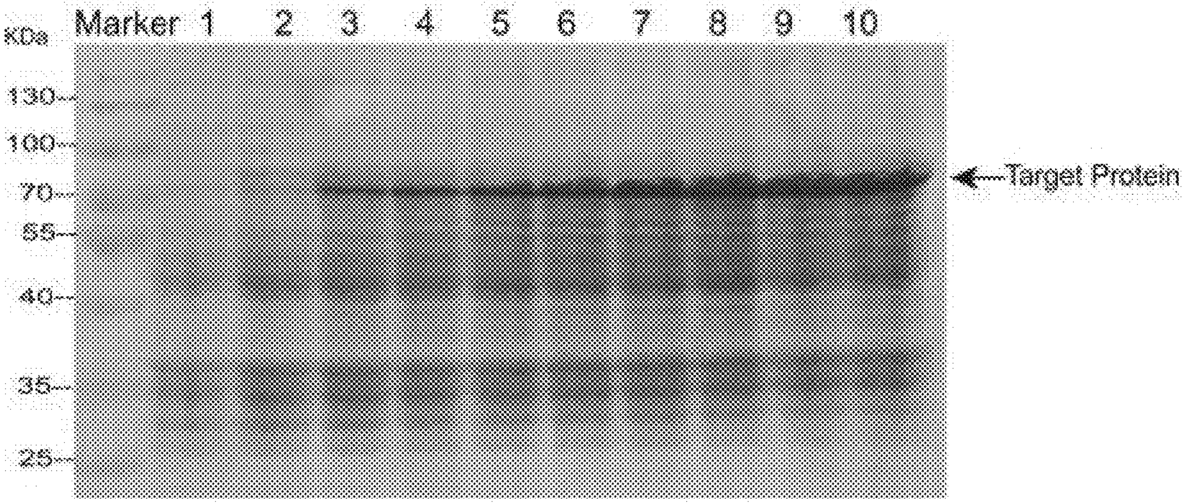
FIG. 5 is a diagram of expression levels of target protein His-HSP65-$6MOG_{35-55}$ at different induction time points by 12% SDS-PAGE electrophoresis.

When the proliferation of the engineering bacteria in step III enters the logarithmic growth period, a sterile lactose solution of 0.5 mol/L is added until the final concentration is 5 mmol/L, and induction culture is conducted at 37° C. Before and after lactose induction for 1 h, 2 h, 3 h, 4 h, 5 h, 6 h, 7 h and 8 h, 1 ml of samples are taken respectively for 12% SDS-PAGE electrophoretic analysis. In FIG. 5, lane 1 shows the total protein expressed in transfected *Escherichia coli* BL21 for pET28a plasmid without lactose induction; lane 2 shows the total protein in transfected *Escherichia coli* BL21 for His-HSP65-$6MOG_{35-55}$ plasmid without lactose induction; and lanes 3-10 show the total protein expression levels of His-HSP65-$6MOG_{35-55}$ transfected *Escherichia coli* BL21 after lactose induction for 1 h, 2 h, 3 h, 4 h, 5 h, 6 h, 7 h and 8 h. As shown in FIG. 5, the expression level of the recombinant protein is increased with the increase of culture time in the first 7 h, and the expression level is not increased significantly later. Therefore, we chose to add an inducer and continue the culture for 7 h (lane 9) to collect mycoprotein.

V. Fermentation Culture of Recombinant Engineering Bacteria and Isolation, Purification and Renaturation of Fusion Protein his-HSP65-6MOG$_{35-55}$ After strain activation and transfer, a sterile lactose solution of 0.5 mol/L is added at the logarithmic growth period until a final concentration of 5 mM/L for induction. After further culture for 7 hours, centrifugal is conducted at 4° C. and 6000 rpm for 20 minutes, and the bacteria are collected. The weight of wet bacteria per 1 L of culture medium is about 12 g, and the bacteria are frozen and preserved at −80° C.

Figures 6A, 6B:
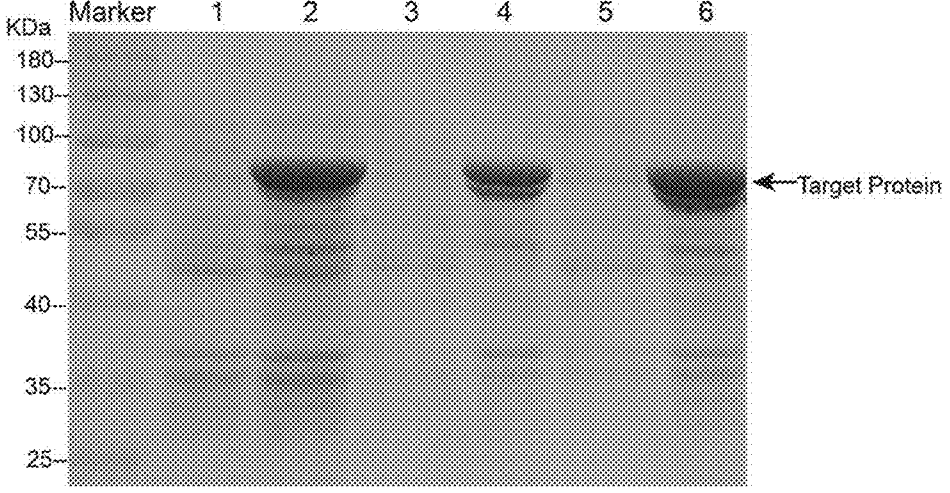
FIG. 6A shows 12% SDS-PAGE analysis expressed by recombinant protein His-HSP65-$6MOG_{35-55}$ after induction and lysis.
FIG. 6B shows Western blot identification of anti-His tag of recombinant protein His-HSP65-$6MOG_{35-55}$.

Every 1 g of the wet bacteria obtained above is suspended in 20 mL of bacteria lysis buffer solution (Tris-HCl buffer solution of 20 mmol/L, and EDTA of 5 mmol/L, with a pH of 8.0) and mixed fully and evenly, and Triton X-100 is added until the final concentration is 0.5%. Ultrasonication is conducted on ice (with a power of 900 W×60%, ultrasonic treatment of 3 s, and rest of 3 s) for crushing for 20 min. Ultransonic lysate is centrifuged at 4° C. and 12000 rpm for 20 min, supernatant and precipitate are collected respectively, and 12% SDS-PAGE protein electrophoretic analysis is conducted to determine the expression form of fusion protein. As shown in FIG. 6A, the target protein is mainly expressed in the precipitate (lane 4), i.e., in the form of inclusion bodies.

The inclusion bodies are treated by washing and urea denaturation. Each gram by wet weight of inclusion bodies is successively washed with 20 mL of washing solution I (Tris-HCl buffer solution of 20 mmol/L, with a pH of 8.0), washing solution II (urea of 2 mol/L dissolved in Tris-HCl buffer solution of 20 mmol/L) and washing solution III (1% Triton X-100 dissolved in Tris-HCl buffer solution of 20 mmol/L). Each gram by wet weight of the inclusion bodies is added into 40 mL of inclusion body denature reagent (urea of 8 mol/L, Tris-HCl buffer solution of 20 mmol/L, NaCl of 500 mmol/L, and imidazole of 5 mmol/L, with a pH of 8.0), and stirred at 4° C. for more than 6 h. The precipitate is denatured and dissolved. Most of the target protein after urea denaturation is dissolved in the supernatant (lane 6 in FIG. 6A). Centrifugation is conducted at 12000 rpm for 20 min, the supernatant is collected and the target protein is purified by Ni-NTA agarose gel column.

The target protein is purified by the Ni-NTA agarose gel column: ddH$_2$O is used for washing thoroughly to wash off 20% ethanol and air in the matrix, and then 50 mM NiSO$_4$ with 5 times of column volume is used for charging. After washing with ddH$_2$O of 5 times of column volume, Binding Buffer (8M urea, Tris-HCl of 20 mM, and NaCl of 0.5M, with pH of 8.0) with 5-10 times of column volume is used for balancing. The target protein supernatant is filtered with a 0.45 μm filter membrane, and then added into Ni-NTA. Impure protein is washed out thoroughly with balance solution of 5 times of column volume (Binding Buffer), and imidazole solution of 10 mM, and the target protein is eluted by imidazole of 100 mM to obtain the required target protein solution. The collected protein solution containing high-purity target protein is further diluted and renaturated, and desalted by dialysis with distilled water at 4° C. The desalted protein solution is pre-frozen overnight at −20° C., and freeze-dried into powder in a freeze dryer. The recombinant protein His-HSP65-6MOG$_{35-55}$ is purified by nickel column, and the target protein is identified by Western Blot, as shown in FIG. 6B.

FIG. 6A shows the determination of the expression form of the target protein His-HSP65-6MOG$_{35-55}$: lane 1 is the total protein before lactose induction of *Escherichia coli* BL21 containing the protein vector plasmid pET28a-His-HSP65-6MOG$_{35-55}$; lane 2 is the total protein after lactose induction of *Escherichia coli* BL21 containing the protein vector plasmid pET28a-His-HSP65-6MOG$_{35-55}$; lane 3 is the lysate supernatant of *Escherichia coli* BL21 transformed by pET28a-His-HSP65-6MOG$_{35-55}$; lane 4 is the lysate precipitate of *Escherichia coli* BL21 transformed by pET28a-His-HSP65-6MOG$_{35-55}$; lane 5 is the precipitate after urea denaturation; and lane 6 is the precipitate supernatant after urea denaturation. FIG. 6B shows Westernblot analysis of recombinant protein His-HSP65-6MOG$_{35-55}$: lane 1 is the total protein of *Escherichia coli* BL21 (DE3) containing plasmid pET28a; lane 2 is recombinant protein His-HSP65-6MOG$_{35-55}$ purified by Ni-NAT column; and lane 3 is freeze-dried powder of His-HSP65-6MOG$_{35-55}$ protein after renaturation.

Figure 7:
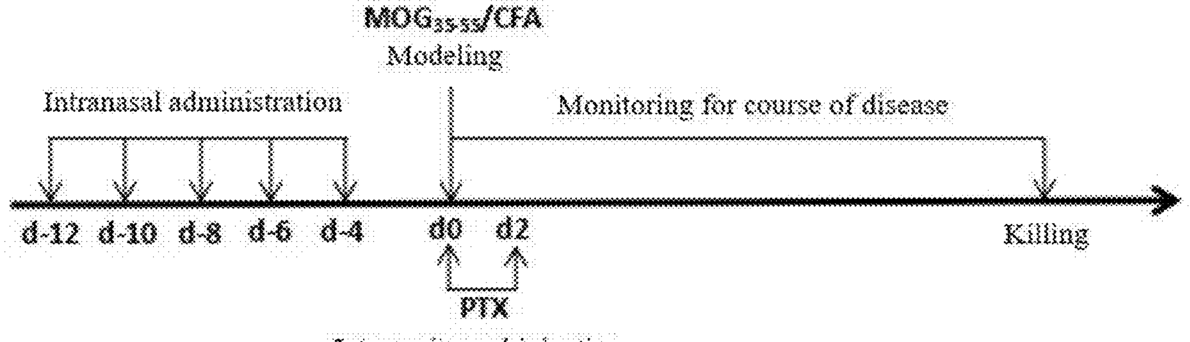
FIG. 7 is an immune flow chart.

VI. Pharmacodynamics Study on Recombinant Protein HSP65-6MOG$_{35-55}$ Obtained Above Female C57BL/6 mice with 6-8 weeks old and 16-20 g of weight are selected, and randomly divided into four groups of A, B, C and D, with 10 mice in each group, wherein A and B groups are administration groups of low dose and high dose of fusion protein vaccines HSP65-6MOG$_{35-55}$, and C group is HSP65 control group; as the control group, HSP65 has the same administration dose and method as A group; D group is PBS control group, and as the control group, PBS has the same administration dose and method as A group. Mucosal administration is performed, and immunization is conducted once every other day for 5 times in total. The specific immune time is shown in FIG. 7. A group, as a low-dose group (100 μg): the recombinant protein is prepared with sterilized PBS to be at concentration of 5 mg/ml, dropped into the nasal cavity, at 20 μl/piece, 10 μl on each side of the nostrils, and 100 μg of protein in total. B group, as a high-dose group (200 μg): the recombinant protein is prepared with sterilized PBS to be at concentration of 10 mg/ml, and the administration step is the same as above. C group is HSP65 control group, and the administration dose is the same as A group. 20 μl of PBS solution is dripped to D group only, with 10 μl in each nostril.

After administration, MS/EAE modeling is conducted for the mice:

PBS solution (3 mg/mL) containing MOG$_{35-55}$ polypeptide (MEVGWYRSPFSRVVHLYRNGK) is fully mixed and emulsified with equal volume CFA through a three-way valve to prepare an emulsion. Subcutaneous injection is conducted through axilla groin at four points. 200 μl of emulsified product (the content of MOG$_{35-55}$ is 300 μg/mouse) is injected in each mouse to prepare an EAE/MS animal model. The day of molding is recorded as day 0 (d0). On the day of immunization (0 h) and the next day of immunization (48 h), mice in each group are provided with pertussis toxin (PTX) intraperitoneally for 200 ng/mouse. The pertussis toxin is used to enhance the immunogenicity of MOG$_{35-55}$ to obtain a disease model.

Figure 8:
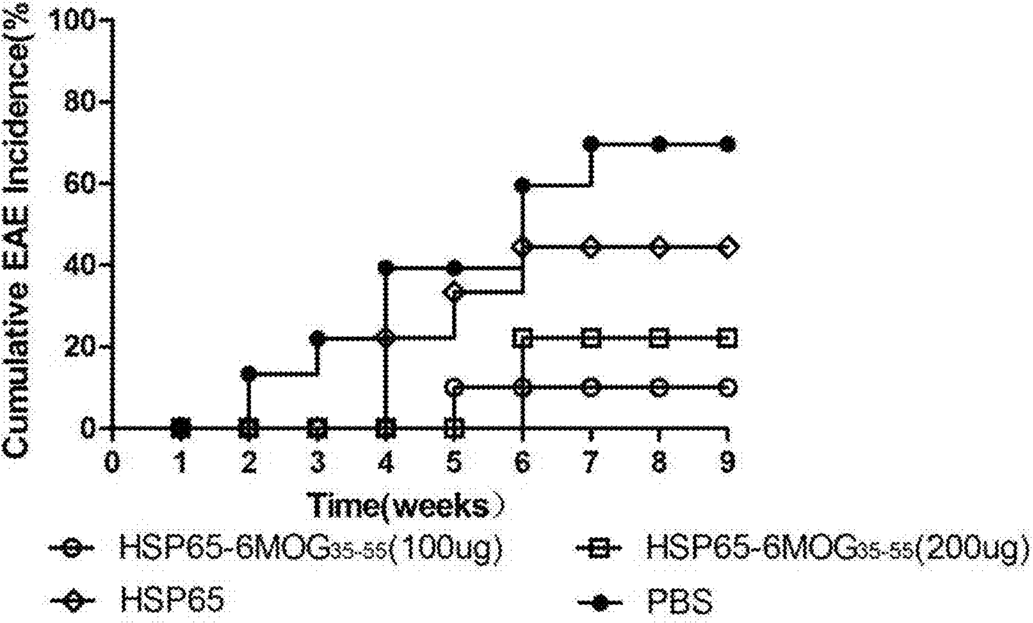
FIG. 8 is a change diagram of incidence of mouse EAE.

The pharmacodynamic results of different groups of mice after immunization are as follows: HSP65-6MOG$_{35-55}$ fusion protein vaccine reduces the incidence of EAE mice. As shown in FIG. 8, the disease of the PBS control group is faster, and the incidence is increased slowly on week 2-week 7, which is consistent with the clinical manifestation of typical chronic progressive EAE. Compared with the PBS control group, the disease time of each administration group is later, and the upward trend of incidence is moderate. HSP65-6MOG$_{35-55}$ (100 μg) group has the disease on week 5, and the incidence on week 9 is 10% (one mouse). HSP65-6MOG$_{35-55}$ (200 μg) group has the disease on week 7, and the incidence is 20% (two mice). HSP65 group has the disease on week 4, and the incidence on week 9 is 44.4% (four mice). The experimental results show that compared with the PBS group, HSP65-6MOG$_{35-55}$ fusion protein vaccine and the HSP65 group can significantly delay the disease of mouse EAE and reduce the incidence, but the effect of HSP65-6MOG$_{35-55}$ group is better than that of the HSP65 group, and the low-dose 100 μg group has the best effect.

Figure 9:
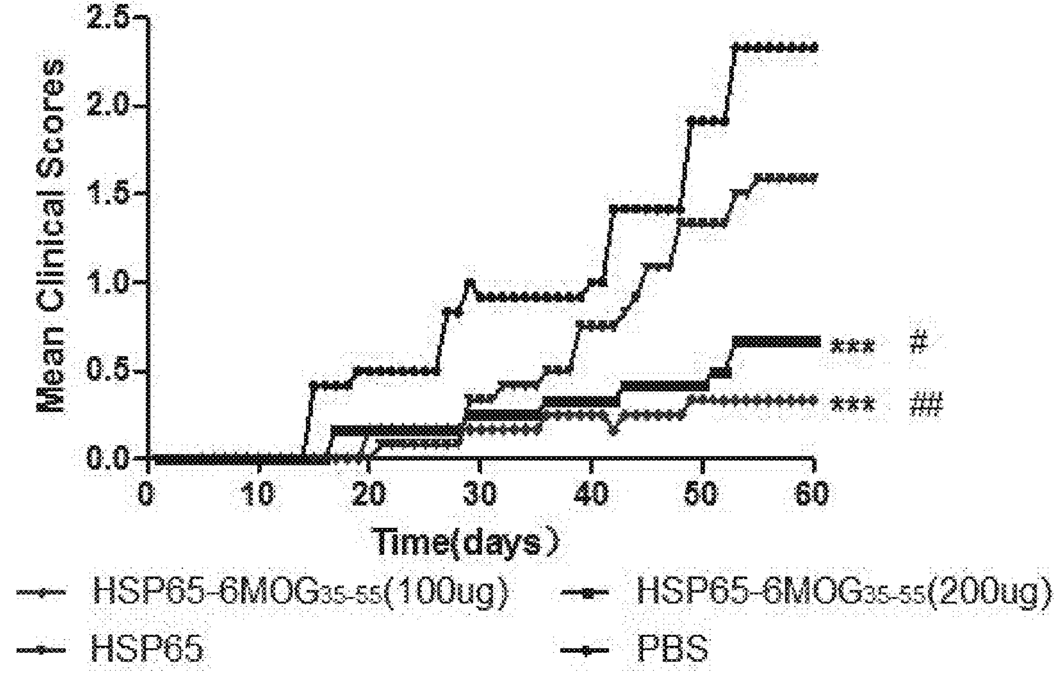
FIG. 9 is a change diagram of clinical scores of mouse EAE.

The HSP65-6MOG$_{35-55}$ fusion protein vaccine reduces the clinical scores of EAE mice. As shown in FIG. 9, the PBS control group has the clinical symptom from d14, and presents a slow upward trend, which conforms to the clinical manifestation of the chronic progressive MS. The highest clinical score is 2.33±0.21. The HSP65 group has the clinical symptom from d21 and has the highest clinical score of 1.58±0.15, which has no significant difference from the PBS control group. The HSP65-6MOG$_{35-55}$ (100 μg) group has the clinical symptom from d20 and has the highest clinical score of 0.33±0.21, which has extremely significant differences from the PBS control group (P<0.001) and has extremely significant differences from the HSP65 group (P<0.01). In FIG. 9, ***P<0.001 indicates comparison with the PBS group; #P<0.05 indicates comparison with the HSP65 administration group; and ##P<0.01 indicates comparison with the HSP65 administration group. The HSP65-6MOG$_{35-55}$ (200 μg) group has the clinical symptom from d17 and has the highest clinical score of 0.67±0.33, which has extremely significant differences from the PBS control group (P<0.001) and has significant differences from the HSP65 group (P<0.05). The experimental results show that HSP65-6MOG$_{35-55}$ (100 μg) and HSP65-6MOG$_{35-55}$ (200 μg) can significantly reduce the scores of mouse EAE, and the mean clinical scores of the two groups have no statistical difference, but the low-dose HSP65-6MOG$_{35-55}$ (100 μg) group has the lowest clinical score.

Figure 10:
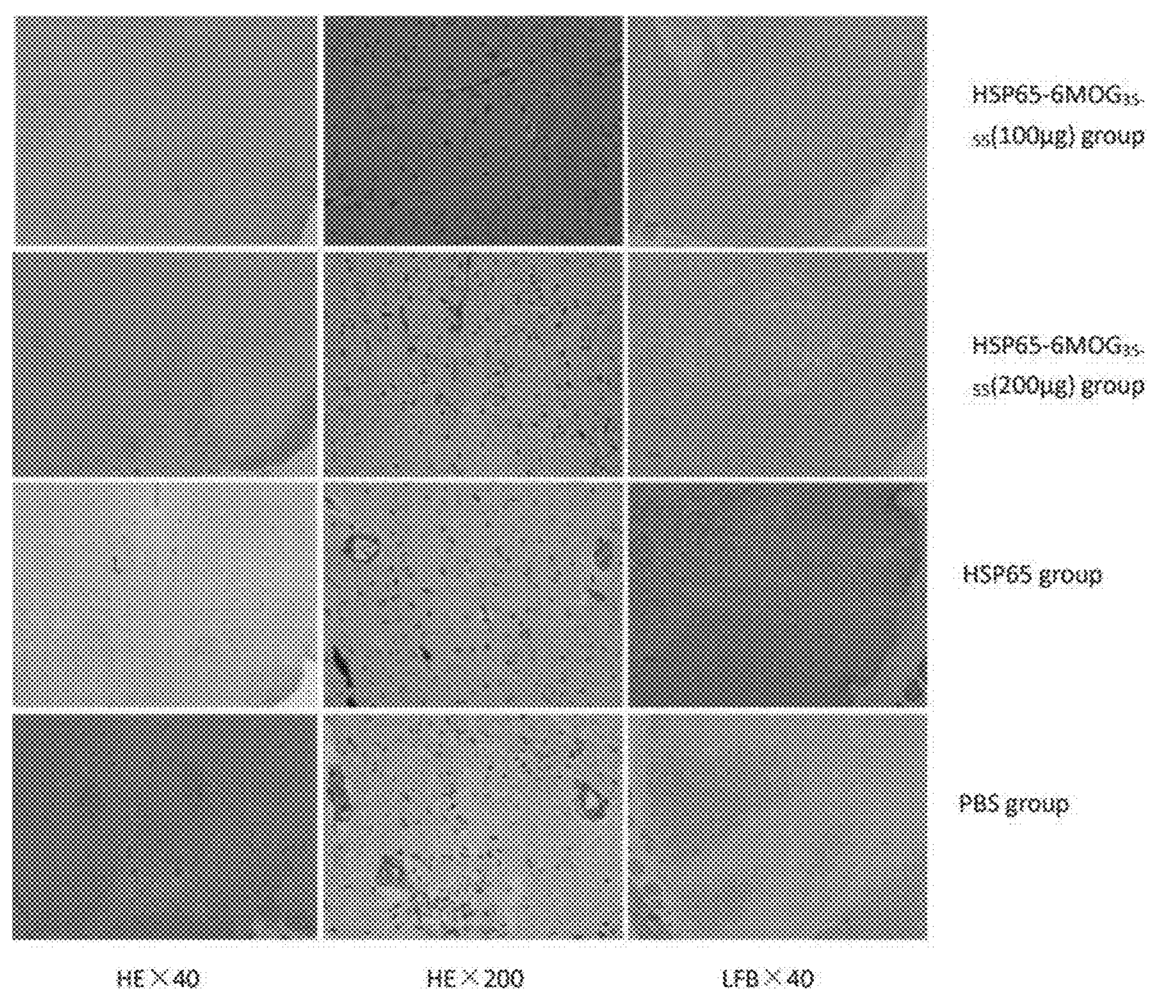
FIG. 10 shows diagrams of HE and LFB staining results of EAE mice.
Figure 11:
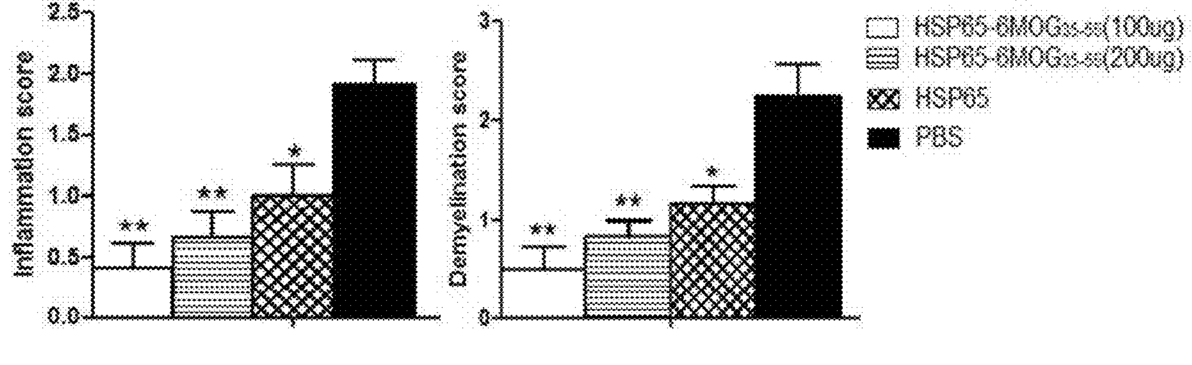
FIG. 11 shows diagrams of inflammation score and demyelination score of EAE mice.

The HSP65-6MOG$_{35-55}$ fusion protein vaccine reduces inflammation and demyelination degree of EAE mice. As shown in FIG. 10, at the end of the experiment, HE staining shows multiple inflammatory lesions in the brain tissue of mice in the PBS control group, and the extensive vascular cuffs are formed by inflammatory cell infiltration. LFB staining shows obvious demyelination lesions and large area loss of blue myelin sheath. The inflammatory demyelination injury in the HSP65 control group is less than that in the PBS control group, but multiple vascular cuffs are still formed. Inflammation and demyelination injury of HSP65-6MOG$_{35-55}$ (200 μg) and HSP65-6MOG$_{35-55}$ (100 μg) are gradually decreased, but have no statistical difference. This indicates that the HSP65-6MOG$_{35-55}$ fusion protein vaccine can significantly reduce the degree of brain inflammation injury and spinal cord demyelination in EAE mice, and the effect of low dose (100 μg) is better. The inflammation score and the demyelination score of the mice in each group are summarized in FIG. 11. In FIG. 11, *P<0.05 indicates comparison with the PBS group; and **P<0.01 indicates comparison with the PBS group.

Figure 12A:
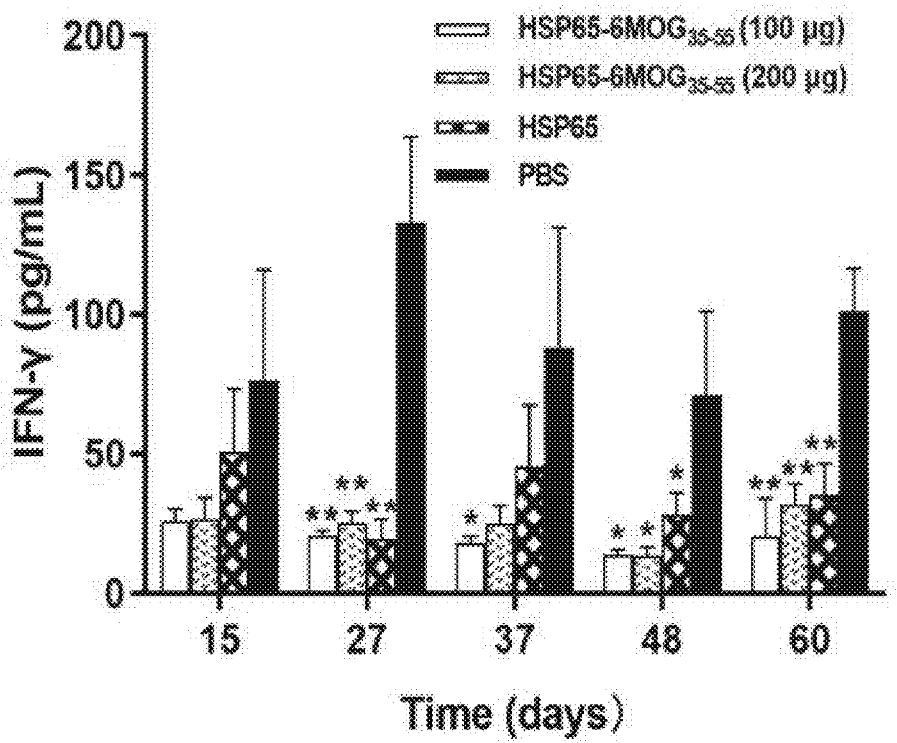
FIG. 12A shows inflammatory cytokine IFN-γ in EAE mice and comparison with a control group in different stages.

The HSP65-6MOG$_{35-55}$ fusion protein vaccine reduces IFN-γ and IL-17A levels of serum inflammatory cytokines. As shown in FIG. 12A, the IFN-γ levels of the PBS control group are apparently higher than those of other administration groups at all stages, have no significant difference on d15, have extremely significant differences (P<0.01) from other groups on d27 and d60, have significant differences (P<0.05) from the HSP65-6MOG$_{35-55}$ (100 μg) group on d37, and have significant differences (P<0.05) from the HSP65-6MOG$_{35-55}$ (100 μg) group, the HSP65-6MOG$_{35-55}$ (200 μg) group and the HSP65 group on d48. The results show that compared with the PBS control group, each administration group can reduce the IFN-γ levels, wherein the HSP65-6MOG$_{35-55}$ (100 μg) group has the best effect. In FIG. 12, *P<0.05 and **P<0.01 indicate comparison with the PBS group; and ##P<0.01 indicates comparison with the HSP65 group.

Figure 12B:
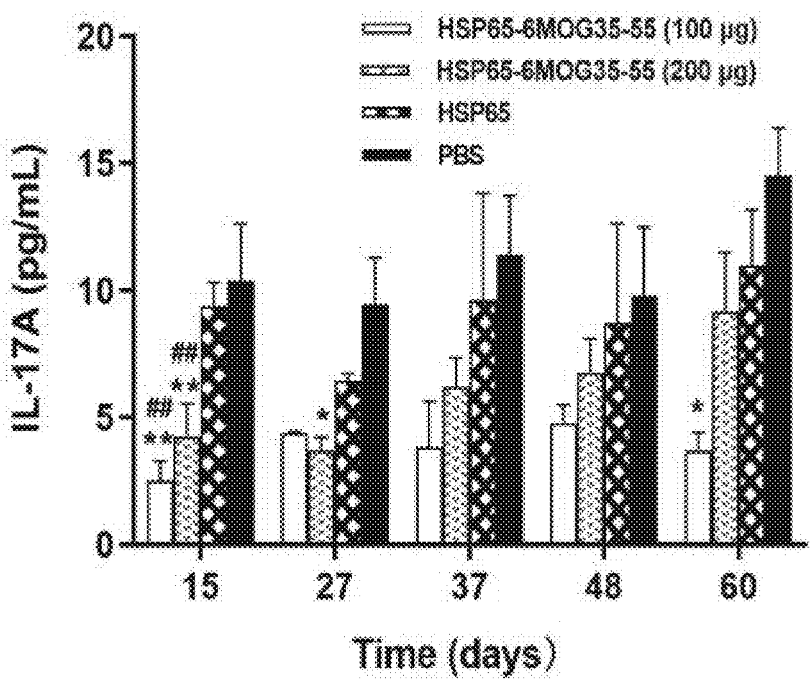
FIG. 12B shows inflammatory cytokine IL-17A in EAE mice and comparison with a control group in different stages.

The IL-17A levels are shown in FIG. 12B. On d15, the HSP65-6MOG$_{35-55}$ (100 μg) group and the HSP65-6MOG$_{35-55}$ (200 μg) group have extremely significant differences (P<0.01) from the HSP65 group and the PBS control group, and in each stage, the HSP65 group and the PBS control group have no significant difference. On d27, the HSP65-6MOG$_{35-55}$ (100 μg) group and the HSP65-6MOG$_{35-55}$ (200 μg) group have significant differences (P<0.05) from the PBS control group. On d60, the HSP65-6MOG$_{35-55}$ (100 μg) group has significant differences (P<0.05) from the PBS control group. The results show that the HSP65 group cannot significantly reduce the IL-17A levels; the IL-17A in the HSP65-6MOG$_{35-55}$ fusion protein vaccine group is at the lowest level in each stage; and the HSP65-6MOG$_{35-55}$ (100 μg) group has the best effect.

In conclusion, the HSP65-6MOG$_{35-55}$ fusion protein vaccine can reduce the incidence of EAE mice, wherein the effect of low dose 100 μg on reducing the incidence of EAE mice is best. The HSP65-6MOG$_{35-55}$ fusion protein vaccine can significantly reduce the clinical scores of EAE mice, and the low-dose HSP65-6MOG$_{35-55}$ (100 μg) group has the lowest clinical score. The HSP65-6MOG$_{35-55}$ fusion protein vaccine reduces the inflammation and demyelination of EAE mice, wherein the effect of low dose (100 μg) on reducing inflammation and demyelination of EAE mice is better. The HSP65-6MOG$_{35-55}$ fusion protein vaccine can reduce IFN-γ and IL-17A levels of serum inflammatory cytokines, wherein the effect of the HSP65-6MOG$_{35-55}$ (100 μg) group is best. To sum up, the recombinant protein HSP65-6MOG$_{35-55}$ of the present invention can play a good role in the prevention of multiple sclerosis through the administration mode of intranasal mucosal immunization.

Other compositions and operation of the recombinant protein capable of resisting multiple sclerosis and the preparation method thereof according to embodiments of the present invention are known to those ordinary skilled in the art, and will not be described in detail.

In the illustration of this description, the illustration of reference terms "embodiment", "example", etc. means that specific features, structures, materials or characteristics illustrated in combination with the embodiment or example are included in at least one embodiment or example of the present invention. In this description, exemplary statements for the above terms shall not necessarily refer to the same embodiment or example. Moreover, the described specific features, structures, materials or characteristics can be combined appropriately in any one or more embodiments or examples.

Although embodiments of the present invention have been shown and described, it will be appreciated for those ordinary skilled in the art that various changes, modifications, replacements and variations can be made to these embodiments without departing from the principle and spirit of the present invention, and the scope of the present invention is limited by the claims and the equivalent thereof.

What is claimed is:

1. A recombinant fusion protein, comprising

HSP65 protein and a 6-segment tandem repeat of myelin oligodendrocyte glycoprotein epitope ($6MOG_{35-55}$), wherein the HSP65 protein and the $6MOG_{35-55}$ are connected through an Ala-Ser-Ala linker and wherein the sequence of the recombinant fusion protein is SEQ ID NO.1.

2. A method of preparing the recombinant fusion protein of claim 1, comprising:

(1) transforming bacterial cells with a recombinant pET28a plasmid comprising the gene encoding the recombinant fusion protein of claim 1 fused to a His tag to obtain engineer ed bacteria having the recombinant plasmid;

(2) culturing the engineered bacteria in LB culture medium until the bacteria reach a logarithmic growth period; adding a sterile lactose solution of 0.5 mol/L into the culture medium to reach a final lactose concentration of 5 mmol/L; and further culturing the bacteria for 7 additional hours; and, collecting the bacteria;

(3) separating and purifying the recombinant fusion protein from the collected bacteria.

3. The method of claim 2, wherein step (1) comprises:

inserting the $6MOG_{35-55}$ gene into a pET-28a (+) vector to obtain a pET28a-$6MOG_{35-55}$ plasmid;

conducting PCR amplification on a template of the pET28a-$6MOG_{35-55}$ plasmid to obtain a target gene segment encoding $6MOG_{35-55}$;

digesting a pET28a-His-HSP65-6P277 vector with NheI and HindIII restriction enzymes to obtain a linearized cloning vector;

recombining the target gene segment encoding $6MOG_{35-55}$ and the linearized cloning vector to obtain the recombinant plasmid; transforming the recombinant plasmid into a competent cell and selecting a positive clone by PCR; and verifying the obtained positive clone to obtain the engineer ed bacteria having the recombinant plasmid.

4. The method of claim 2, wherein step (3) comprises:

lysing and ultrasonically breaking the collected bacteria on ice to obtain inclusion bodies comprising the recombinant fusion protein;

processing the inclusion bodies with an inclusion body solution containing urea;

collecting the supernatant; and purifying the recombinant fusion protein with a Ni-NTA agarose gel column to obtain the recombinant fusion protein comprising His-HSP65-$6MOG_{35-55}$.

* * * * *